United States Patent [19]

Laura et al.

[11] 4,303,592
[45] Dec. 1, 1981

[54] AMIDINOPHENYLMETHYLSULFONYL-FLUORIDE

[75] Inventors: Richard Laura, Somerville; David H. Bing, Brookline, both of Mass.

[73] Assignee: Center for Blood Research, Inc., Boston, Mass.

[21] Appl. No.: 110,592

[22] Filed: Jan. 9, 1980

[51] Int. Cl.³ ............................................. C07C 143/70
[52] U.S. Cl. ................................... 260/543 F; 435/23; 435/184; 435/213; 435/214; 435/219
[58] Field of Search .............. 260/543 F; 435/23, 184, 435/213, 214, 219

[56] References Cited

U.S. PATENT DOCUMENTS 3,920,738  11/1975  Martin .............................. 260/543 F
4,001,087  1/1977   Wong et al. ........................... 435/23

Primary Examiner—Natalie Trousof
Assistant Examiner—Vera C. Clarke
Attorney, Agent, or Firm—Wolf, Greenfield & Sacks

[57] ABSTRACT

A new compound amidinophenylmethylsulfonylfluoride is formed and preferably used in the para isomer form as an irreversible inactivator of selected serine proteases.

7 Claims, 2 Drawing Figures

AMIDINOPHENYLMETHYLSULFONYLFLUORIDE

BACKGROUND OF THE INVENTION

Several materials are known which inactivate serines proteases. Such inactivators can be used for various purposes including affinity labeling of serine proteases to isolate and identify active site sequences, manufacture of plasma proteins and inactivation of certain enzymes in tissue culture. One of the best irreversible inhibitors presently used for serine protease inactivation is diisopropylfluorophosphate (DFP). This material while highly reactive and useful has been found to have drawbacks. It can enter the body of the user by inhalation or cutaneous absorption. Even trace amounts of DFP cause severe miosis while large quantities can cause irreversible inactivation of acetylcholinesterase leading to vomiting, muscle cramps and even death. This makes DFP extremely toxic and dangerous to handle and use. DFP is relatively unstable and can decompose upon exposure to moisture forming hydrogen fluoride which itself causes certain dangers. These toxic properties of DFP have led to its use as a nerve gas in chemical-biological warfare. In contrast the reaction of DFP with serine proteases is often slow and large molar excesses must be used to obtain complete enzyme inactivation.

Phenylmethanesulfonylfluoride, another known serine protease inactivator material is less toxic and more stable than DFP, but like DFP, is also non-selective in that it inhibits both trypsin and chymotrypsin and must be used in large excess with respect to the enzyme to be inactivated. It is known that fast inactivation times and minimized amounts of reactants are preferred in order to speed up processing and to introduce small amounts of materials in certain procedures while minimizing volumes and costs in other procedures.

Certain other sulfonyl fluoride compounds have previously been described for possible use as serine protease inhibitors, Acta Biol. Med. Germ. 28, 577–585 [1972] "Inaktivierung von Trypsin und Thrombin durch 4-Amidinobenzolsulfofluorid und 4-(2-Aminoäthyl)-benzosulfofluorid", P. Walsmann, M. Richter and F. Markwardt, describes such materials. However, the materials described are not the specific compounds of this invention and do not have the reactivity and usefulness of the compounds of this invention.

SUMMARY OF THE INVENTION

It is an object of this invention to provide new and useful compounds in the form of isomers of amidinophenylmethylsulfonylfluoride.

It is another object of this invention to provide serine protease inhibitors which are highly useful in inactivation of proteases, react in low molar to molar ratios, are relatively safe to handle and use and/or can be selective in inactivating only certain proteases.

It is still another object of this invention to provide uses of the compounds of the preceding objects which uses are in replacing other known serine protease inactivators in a plurality of known methods.

According to the invention, a new and useful compound is provided which acts as a selective serine protease inactivator and is amidinophenylmethylsulfonylfluoride. Preferably p-amidinophenylmethylsulfonylfluoride is used since it has higher activity than the meta form and can easily be synthesized. The ortho form is more difficult to produce by known synthetic methods and may not have all of the desired properties.

According to the method of this invention, the amidinophenylmethylsulfonylfluoride isomers can be used in many applications where serine protease inhibitors have hithertofore been used. For example, the compound is useful for determining amino acid sequence of certain proteins. It can also be used to inactivate serine proteases in tissue culture.

It is a feature of this invention that amidinophenylmethylsulfonylfluoride can be synthesized in the para form (PAPMSF) as well as other forms using conventional methods. PAPMSF is selective and thus irreversibly inactivates several serine proteases while it is inactive against other serine proteases making it useful as a selective irreversible inhibitor.

The material, particularly in the para form, is highly reactive, reacts selectively and rapidly under physiological conditions on substantially a molar to molar basis. It reacts with trypsin but not chymotrypsin and thus apparently specifically inhibits proteases which have a benzamidine binding site. Reactions are rapid and require only a slight excess of reagent. The material is a stable solid at room temperature and can be easily and safely handled.

BRIEF DESCRIPTION OF THE DRAWINGS

The above and other features, objects and advantages of the present invention will be better understood from a reading of the following specification in conjunction with the attached drawings in which:

FIG. 1 is a graphic example illustrating the Inactivation of Serine Proteases and acetylcholinesterase by PAPMSF; and FIG. 2 is a graphic example illustrating Inactivation of Trypsin by m-amidniophenylmethylsulfonylfluoride (MAPMSF).

DESCRIPTION OF PREFERRED EMBODIMENTS

Amidinophenylmethylsulfonylfluoride has the following formula in the ortho, meta and para form:

PAPMSF:

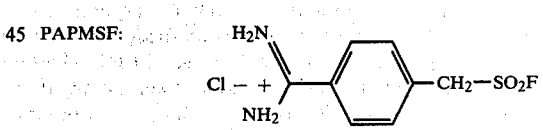

MAPMSF:

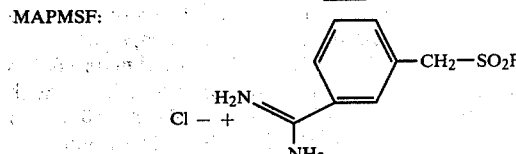

OAPMSF:

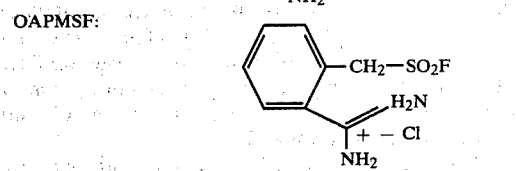

The para form will be referred to for the most part here since it is easiest to synthesize when compared to the ortho form and more reactive than the meta form for the purposes of this invention. A preferred method for synthesis of PAPMSF is described in Example 1. The ortho material has not been synthesized as yet.

The following Examples are meant to illustrate forms of the invention and are not to be considered as limiting thereof.

EXAMPLE 1

A mixture of α-bromo-p-tolunitrile (24.5 g; 125 mmol) and sodium sulfite (17.0 g; 135 mmol) in 50 ml of water was heated to reflux and refluxed for 18 hours. The mixture was poured, while still hot, into 100 ml of saturated aqueous NaCl. The resulting heavy white precipitate was thoroughly chilled, collected by suction filtration, and washed with two portions of saturated aqueous NaCl and three portions of Et$_2$O. After drying in vacuo over CaSO$_4$, the sodium p-cyanophenylmethylsulfonate was obtained in essentially quantitative yield.

In a dry 500 ml roundbottom flask containing a stir bar was prepared, a suspension of sodium p-cyanophenylmethyl sulfonate (11.0 g; 50 mmol) in 150 ml of anhydrous tetrahydrofuran (THF). Anhydrous methanol (4.0 ml; 3.2 g; 100 mmol) was added and the suspension was cooled in an ice bath. Anhydrous HCl was bubbled into the cold suspension in a rapid stream for 90 minutes and the mixture was then stirred at 4° for four days. THF and excess HCl were removed under reduced pressure on a rotary evaporator leaving a creamy residue. The residue was suspended in anhydrous methanol (150 ml) and the mixture was stirred at room temperature while methanolic ammonia was added dropwise until the mixture was neutral (as determined with pH paper). The mixture was heated in an oil bath and kept at a bath temperature of 60°-65° for about 3 hours. The pH was checked occasionally and additional methanolic ammonia was added if required to maintain neutrality. After cooling to room temperature, the mixture was stored in a freezer for two days to allow complete precipitation. The precipitate was collected by suction filtration and was washed with EtOAc. After drying in vacuo, the crude ammonium p-amidinophenylmethylsulfonate hydrocholoride amounted to 10.7 g (39 mmol; 78%).

In a 100 ml roundbottom flask containing a stir bar and equipped with a reflux condenser and CaCl$_2$ drying tube was prepared a mixture of dry ammonium p-amidinophenylmethylsulfonate hydrochloride (10.7 g; 39 mmol) and phosphorous oxychloride (50 ml). The mixture was heated in an oil bath and was kept at a bath temperature of 80° (±3°) for 18 hours. After cooling to room temperature, volatile materials were removed under reduced pressure on a rotary evaporator. The residue was mixed with Et$_2$O and the solid material was collected by suction filtration and was washed with Et$_2$O. The solid was dissolved in about 250 ml of CH$_3$CN containing 1 ml POCl$_3$, filtered by gravity, and the filtrate was concentrated until a dense precipitate had formed. This precipitate was collected by suction filtration, washed with Et$_2$O and dried in vacuo. The yield of p-amidinophenylmethylsulfonyl chloride hydrochloride was 4.2 g (15.6 mmol; 31% from sodium p-cyanophenylmethylsulfonate).

In a 50 ml roundbottom flask containing a stir bar was prepared a mixture of the sulfonylchloride (1.0 g; 3.7 mmol) and sodium fluoride (0.5 g; 11.9 mmol) in CH$_3$CN (30 ml). The flask was fitted with a reflux condenser and CaCl$_2$ drying tube and the mixture was gently refluxed for 16 hours. After cooling, the mixture was filtered by gravity and the filtrate was concentrated to dryness under reduced pressure on a rotary evaporator. The solid was dissolved in approximately 30 ml of acetone, 60 ml of 1% aqueous HCl was added and the solution was concentrated to a small volume under reduced pressure on a rotary evaporator. After chilling, the product was obtained as fluffy white needles which were collected by suction filtration, washed with CH$_2$Cl$_2$ and dried vacuo. The yield of p-amidinophenylmethylsulfonyl fluoride hydrochloride, mp 190°-191°, was 0.4 g (1.6 mmol; 43%).

The synthesis is set forth below:

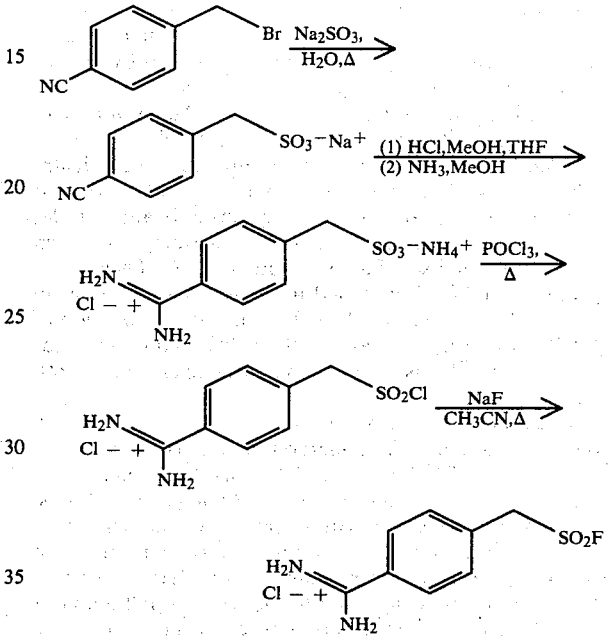

The PAPMSF and other isomers are stable in the form of salts formed with the conjugate base of any organic or inorganic acid. The chloride salt form is preferred but other useful salts including but not limited to are the bromide, iodide, toluene sulfonate, picrate and benzene sulfonate. Salts of PAPMSF have good stability at physiological conditions including pH and contact with aqueous based body fluids thus enhancing usefulness. Although the salts are used the materials of this invention will be referred to herein as pure compounds, i.e., amidinophenylmethylsulfonylfluoride, for convenience and as is customary in the art.

EXAMPLE 2

Meta amidinophenylmethylsulfonylfluoride can be obtained in an analogous fashion to Example 1 substituting only α-bromo-m-tolunitrile for the α-bromo-p-tolunitrile used.

Example 3 below indicates a synthesis scheme which could be used to prepare o-amidinophenylmethylsulfonylfluoride.

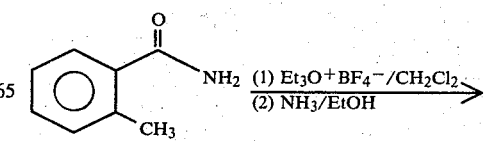

1

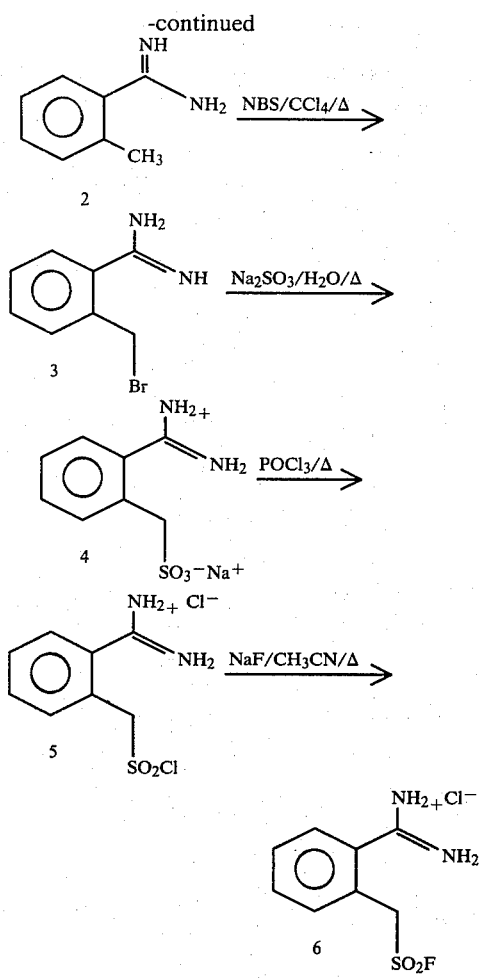

Reaction of o-toluamide 1 commercially available, or prepared as described: Noller, *Organic Syntheses*, Collective Volume II, 586 (1943); Hauser, Hoffenberg, *J. Org. Chem.*, 20, 1448 (1955), with triethyloxonium fluoroborate in $CH_2Cl_2$ and treatment of the intermediate imidate fluoroborate with ethanolic ammonia as described by Weintraub and coworkers, L. Weintraub, S. R. Oles, and N. Kalish, *J. Org. Chem.*, 33, 1679 (1968), provides o-toluamidine 2. Benzylic bromination of 2 using an equivalent of N-bromosuccinimide in $CCl_4$ yields 3, which is converted to sulfonate 4 upon treatment with aqueous sodium sulfite. Conversion of 4 to sulfonyl chloride 5 and ultimately to o-amidinophenylmethylsulfonylfluoride 6 is accomplished by the reactions previously described for the para isomer.

EXAMPLE 4 p-Amidinophenylmethylsulfonylfluoride was tested for inhibitory activity against several serine proteases and acetyl cholinesterase. The enzymes used in the inhibition studies were obtained from commercial sources or were purified by literature procedures. Enzymatic activity was assayed by standard methods. At neutral pH, with approximately a 10-fold excess of reagent over enzyme, p-amidinophenylmethylsulfonylfluoride rapidly inactivated bovine trypsin, human thrombin, and human $\overline{Clr}$ and $\overline{Cls}$, subcomponents of the first component of complement. These proteases have in common anionic binding sites which are known to bind benzamidine. In contrast, bovine chymotrypsin, a serine protease and bovine acetyl cholinesterase, both of which do not possess a benzamidine binding site, were not inhibited by p-amidinophenylmethylsulfonylfluoride under similar conditions. These results are shown in FIG. 1. Even at lower concentrations (approximately 2:1 reagent:enzyme), p-amidinophenylmethylsulfonylfluoride was still an effective inhibitor (Table 1). p-Amidinophenylmethylsulfonylfluoride does not react with acetyl cholinesterase and thus does not have the toxic properties previously described for diisopropylfluorophosphate.

TABLE 1

| Enzyme | [PAPMSF] μM | % Activity Remaining at Time (min) | | |
|---|---|---|---|---|
| | | 1 | 5 | 10 |
| Trypsin, 60.6 μM | 127 | 0 | 0 | 0 |
| Thrombin, 74.5 μM | 159 | 26 | 24 | 21 |
| $\overline{Cls}$, 27.5 μM | 64 | 60 | 59 | 52 |
| $\overline{Clr}$, 4.8 μgm/ml | 130 | — | — | 25 |

In further experiments with trypsin, the rate of inactivation of trypsin by p-amidinophenylmethylsulfonylfluoride was shown to be essentially unchanged if the reaction was carried out at pH 3.0, 5.0 or 7.4. In addition, dialysis of inactivated trypsin did not lead to recovery of enzymatic activity, confirming the irreversible nature of the inactivation reaction. Estimates of the rate constants for inactivation under pseudo-first-order conditions are: trypsin, $58 \times 10^{-3}$ sec$^{-1}$; thrombin, $26 \times 10^{-3}$ sec$^{-1}$; $\overline{Cls}$, $8 \times 10^{-3}$ sec$^{-1}$.

FIG. 2 shows inactivation of trypsin by meta amidinophenylmethylsulfonylfluoride.

m-Amidinophenylmethylsulfonylfluoride was tested for inhibitory activity against bovine trypsin and chymotrypsin. Chymotrypsin showed no loss of activity when incubated for 30 minutes with a four-fold molar excess of m-amidinophenylmethylsulfonylfluoride. Trypsin was slowly inactivated in the presence of equimolar or greater amounts of this reagent.

PAPMSF is a white, crystalline solid with a melting point of 190° C. It is stable in solution in organic solvents such as methanol, acetone, ethanol, dimethylsulfoxide, acetonitrile, dimethylformamide and the like. It is soluble in water up to $10^{-2}$ molar and is preferably reactive at physiological conditions such as pH's of from about 5 to about 7.5.

Reactions are preferably carried out at a pH of around 6 to 7.5 at temperatures of from 20° C. to 40° C.

Suitable solvents for use of PAPMSF and the ortho and meta isomers can be any polar organic materials preferably at PAPMSF concentrations of from 0.01 Molar to 0.1 Molar. Aqueous solutions above pH 8 are not preferred since the PAPMSF can hydrolyze to sulfonic acid in water at high pH.

Uses of the materials of this invention include affinity labeling of serine proteases, the manufacture of a variety of plasma protein, titration of proteases and the inactivation of enzymes to promote tissue culture. The materials of this invention can be used to replace serine protease inactivators in any use where DFP has previously been used and in which the enzyme binds benzamidine at the active site. This would include virtually all of the known plasma serine proteases. For example, the amidinophenylmethylsulfonylfluorides of this invention can be used to purify clotting proteins as described with respect to DFP in *A Comparison of Human Prothrombin, Factor IX (Christmas Factor) Factor X*

(Stuart Factor and Protein S), R. G. D. Scipio, M. A. Hermodson, S. B. Yate and E. W. Davie, Biochemistry 16:698-706, 1977. Still another use is the purification of C1 inactivator as described in *A Simplified Procedure For Purification of C1 Inactivator from Human Plasma*, A. Reboul, G. J. Arland, R. B. Sim and M. G. Colomb, FEBS Letters 79:45050, 1977. The purification of C1 proteins can also be carried out with the materials of this invention using these materials as stabilizers of the proteins to make isolation easier as described with respect to DFP in *The Unactivated Form of the First Component of Human Complement C1*, I. Gigli, R. R. Porter, and R. B. Sim, Biochemical J. 157:541-548, 1976. In each of the above procedures, the PAPMSF is substituted for the DFP used.

Outlined below as Example 5 is a proposed plan for an amino acid sequence study using PAPMSF.

EXAMPLE 5

The aim of these proposed studies is to determine the amino acid sequence of those portions of the peptide chains of C1r̄ and C1s̄ which react(s) with PAPMSF.

(1) PAPMSF Reactive Site

The information on the amino acid sequence at the site of reaction of PAPMSF is known for plasmin and thrombin and a similar analysis has been reported for C1s̄ but no data presented. No such studies have been done with C1r̄. These data are summarized in the Table below; trypsin and chymotrypsin are presented for comparison. The particular residue of interest is the one analogous to Gln 192 in trypsin. Based on analysis of a computer model of the X-ray crystallographic structure of trypsin, this residue is directly involved in interactions at the meta position on the benzamidine ring and in determining the substrate specificity of the pancreatic serine proteases (Kraut, J. Ann Rev. Biochem. 46:331, 1977; Feldmann, R. J., Bing, D. H., Furie, B. C. and Furie, B., Proc. Natl. Acad. Sci. 75:5409, 1978; Andrews, J. M., Roman, D. P., Jr., Bing, D. H. and Cory, M., J. Med. Chem. 21:1202 [1978]). It thus becomes important to determine the amino acid at this position in C1r̄ and C1s̄. To do this, advantage will be taken of cysteines at position 191 and at 201 (in plasmin) or 220 (as in thrombin) which are conserved in mammalian serine proteases because of their critical role in determining the stereochemistry of the binding pocket; in the case of trypsin, thrombin and presumably plasmin and C1s̄, this binding pocket contains an aspartic acid (189) which leads to ionic interaction with benzamidine inhibitors or lysine/arginine residues in protein substrates.

TABLE 2

SEQUENCE OF ACTIVE SITE OF SERINE PROTEASES

| Residue #[a] | 188 | 189 | 190 | 191 | 192 | 193 | 194 | 195 | 196 | 197 | 198 | 199 | 200 | 201 | ... 220 |
|---|---|---|---|---|---|---|---|---|---|---|---|---|---|---|---|
| Chymotrypsin | Val | Ser | Ser | Cys | Met | Gly | Asp | Ser | Gly | Gly | Pro | Leu | Val | Cys | ... |
| Trypsin | Lys | Asp | Ser | Cys | Gln | Gly | Asp | Ser | Gly | Gly | Pro | Val | Val | Cys | ... |
| Thrombin | Gly | Asp | Ala | Cys | Glu | Gly | Asp | Ser | Gly | Gly | Pro | Phe | Val | Met | ... Cys |
| Plasmin |  | Ser | Cys | Gln | Gly | Asp | Ser | Gly | Gly | Pro | Leu | Val | Cys |  |  |
| C1s̄ |  |  | Ala | Cys | Gly | Lys | Asp | Ser | Gly | Gly | Arg |  |  |  |  |

[a]Numbering system of chymotrypsin is used.

To sequence the active site of C1r̄ and C1s̄ in this region the following steps will be taken:

i. Stoichiometric label with PAPMSF followed by reaction with $^{35}S$—$Na_2SO_3$ in the presence of base. The reaction with $^{35}S$—$Na_2SO_3$ has not been successfully carried out as yet in limited experimentation. However, other labels could be used or the PAPMSF could be made as a label itself if necessary. In the case of $Na_2SO_3$, the labeled active site serine is converted to cysteic acid in which the sulfur is radiolabeled.

ii. Isolation of the light chains of C1r̄ and C1s̄ under dissociation-reducing conditions (e.g. 0.1% sodium dodecyl sulfate - 0.1 M mercaptoethanol, pH 7.4) by gel filtration on Sephadex G-100 (Utsumi U. and Karush, F. Biochemistry 3:1329, 1964).

iii. Citraconylation, reduction, aminoethylation and modification with cyclohexandione of the $^{35}S$-light chain. This will block all lysines and arginines and convert the cysteine to a form (aminoethylated) which is sensitive to trypsin digestion (Slobin, L.I., and Singer, S.J. J. Biol. Chem. 243:1777, 1968; Milstein, C. Biochem. J. 101:338, 1966).

iv. Trypsin digestion (with TPCK-treated trypsin) and preliminary separation by gel filtration in 0.1 M $(NH_4)_2CO_3$ ph 7.0 followed by final purification by high voltage electrophoresis at pH 6.5.

v. Amino acid composition will be determined and the sequence determined by the Dansyl-Edman method (Gray W.R. and Smith, J.F. Anal. Biochem. 33:36, 1970). Should additional sensitivity be required, use will be made of [$^{14}C$]dansylchloride to determine the N-terminal amino acid of the peptides (Gray W.R. and Smith, J.F. Anal. Biochem. 33:36, 1970).

The complete modification at each step under neutral conditions should lead to isolation of the cysteine loop which contains the active site serine. This information will be extremely important for gaining insights into the chemical nature of the active sites of these two enzymes.

While specific examples have been shown and described many variations are within the scope of this invention.

What is claimed is:
1. Amidinophenylmethylsulfonylfluoride.
2. p-Amidinophenylmethylsulfonylfluoride.
3. m-Amidinophenylmethylsulfonylfluoride.
4. o-Amidinophenylmethylsulfonylfluoride.
5. p-Amidinophenylmethylsulfonylfluoride in accordance with claim 2 in a salt form.
6. m-Amidinophenylmethylsulfonylfluoride in accordance with claim 3 in a salt form.
7. o-Amidinophenylmethylsulfonylfluoride in accordance with claim 4 in a salt form.

* * * * *